US00PP21588P2

(12) United States Plant Patent
Wood

(10) Patent No.: US PP21,588 P2
(45) Date of Patent: Dec. 28, 2010

(54) ***SPIRAEA* PLANT NAMED 'TRACY'**

(50) Latin Name: ***Spiraea fritschiana*×*Spiraea japonica***
Varietal Denomination: Tracy

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/462,558

(22) Filed: Aug. 5, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Spiraea* plant named 'Tracy', characterized by its upright, outwardly spreading and mounding plant habit; vigorous growth habit; freely branching habit; during the spring, developing leaves are orange red in color and become bright yellow in color with development; during the summer, developing leaves are greyed orange in color and become yellow green in color with development; numerous large dark pink-colored flowers; and good garden performance.

3 Drawing Sheets

Botanical designation: *Spiraea fritschiana*×*Spiraea japonica.*

Cultivar denomination: 'TRACY'.

BACKGROUND OF THE INVENTION

The present invention relates to a new and distinct cultivar of *Spiraea* plant, botanically known as *Spiraea fritschiana*× *Spiraea japonica* and hereinafter referred to by the name 'Tracy'.

The new *Spiraea* plant is a product of a planned breeding program conducted by the Inventor in Grand Haven, Mich. The objective of the breeding program is to develop new *Spiraea* cultivars with attractive leaves and flowers.

The new *Spiraea* plant originated from a cross-pollination in 2003 of *Spiraea fritschiana* 'Wilma', disclosed in U.S. Plant Pat. No. 15,397, as the female, or seed, parent with an unnamed seedling selection of *Spiraea japonica,* not patented, as the male, or pollen, parent. The new *Spiraea* plant was discovered and selected by the Inventor in 2005 as a single flowering plant within the progeny of the stated cross-pollination in a controlled environment in Grand Haven, Mich.

Asexual reproduction of the new *Spiraea* plant by softwood cuttings in a controlled greenhouse environment in Grand Haven, Mich. since the summer of 2005 has shown that the unique features of this new *Spiraea* plant are stable and reproduced true to type in successive generations of asexual reproduction.

SUMMARY OF THE INVENTION

Plants of the new *Spiraea* have not been observed under all possible environmental conditions. The phenotype may vary somewhat with variations in environment and cultural practices such as temperature and light intensity without, however, any variance in genotype. The following traits have been repeatedly observed and are determined to be the unique characteristics of 'Tracy'. These characteristics in combination distinguish 'Tracy' as a new and distinct cultivar of *Spiraea:*

1. Upright, outwardly spreading and mounding plant habit.
2. Vigorous growth habit.
3. Freely branching habit.
4. During the spring, developing leaves are orange red in color and become bright yellow in color with development; during the summer, developing leaves are greyed orange in color and become yellow green in color with development.
5. Numerous large dark pink-colored flowers.
6. Good garden performance.

Plants of the new *Spiraea* can be compared to plants of the female parent, 'Wilma'. Plants of the new *Spiraea* differ from plants of 'Wilma' in the following characteristics:

1. Plants of the new *Spiraea* and 'Wilma' differ in leaf color as plants of 'Wilma' have green-colored leaves.
2. Plants of the new *Spiraea* have darker-colored flowers than plants of 'Wilma'.

Plants of the new *Spiraea* can be compared to plants of the male parent selection. Plants of the new *Spiraea* differ from plants of the male parent selection in the following characteristics:

1. Plants of the new *Spiraea* are larger than plants of the male parent selection.
2. Plants of the new *Spiraea* and the male parent selection differ in developing leaf color as plants of the male parent selection have red-colored developing leaves.
3. Plants of the new *Spiraea* have larger flowers than plants of the male parent selection.

Plants of the new *Spiraea* can be compared to plants of the *Spiraea japonica* 'Gold Flame', not patented. In side-by-side comparisons conducted in Grand Haven, Mich., plants of the new *Spiraea* differed from plants of 'Gold Flame' in the following characteristics:

1. Plants of the new *Spiraea* were larger than plants of 'Gold Flame'.
2. Plants of the new *Spiraea* and 'Gold Flame' differed in developing leaf color as plants of 'Gold Flame' had red-colored developing leaves.

3. Plants of the new *Spiraea* had larger flowers than plants of 'Gold Flame'.
4. Plants of the new *Spiraea* had lighter pink-colored flowers than plants of 'Gold Flame'.

Plants of the new *Spiraea* can also be compared to plants of the *Spiraea japonica* 'Walbuma', disclosed in U.S. Plant Pat. No. 9,363. In side-by-side comparisons conducted in Grand Haven, Mich., plants of the new *Spiraea* differed from plants of 'Walbuma' in the following characteristics:

1. Plants of the new *Spiraea* were faster growing than plants of 'Walbuma'.
2. Plants of the new *Spiraea* not as broad as plants of 'Walbuma'.
3. Plants of the new *Spiraea* and 'Walbuma' differed in leaf color as plants of 'Walbuma' had gold-colored leaves.
4. Plants of the new *Spiraea* were more freely flowering than plants of 'Walbuma'.

BRIEF DESCRIPTION OF THE PHOTOGRAPHS

The accompanying colored photographs illustrate the overall appearance of the new *Spiraea* plant, showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet is a side perspective view of a typical flowering plant of 'Tracy' grown in an outdoor nursery during the summer.

The photograph on the second sheet is a close-up view of a typical vegetative plant of 'Tracy' grown in an outdoor nursery during the spring.

The photograph on the third sheet is a close-up view of typical inflorescences and leaves of 'Tracy'.

DETAILED BOTANICAL DESCRIPTION

The aforementioned photographs and following observations, measurements and values describe plants of the new *Spiraea* grown in an outdoor nursery in Grand Haven, Mich. during the spring and early summer and under conditions which closely approximate commercial production. Plants were three years old when the photographs and the description were taken. In the description, color references are made to The Royal Horticultural Society Colour Chart, 1995 Edition, except where general terms of ordinary dictionary significance are used.

Botanical classification: *Spiraea fritschiana*×*Spiraea japonica* 'Tracy'.

Parentage:

*Female, or seed, parent.*—*Spiraea fritschiana* 'Wilma', disclosed in U.S. Plant Pat. No. 15,397.

*Male, or pollen, parent.*—Unnamed seedling selection of *Spiraea japonica,* not patented.

Propagation:

*Type.*—By softwood cuttings.

*Time to initiate roots.*—About 20 days at 25° C.

*Time to produce a rooted young plant.*—About three months at 25° C.

*Root description.*—Fine to thick, fibrous; cream to brown in color.

*Rooting habit.*—Freely branching; dense.

Plant description:

*Plant form and growth habit.*—Perennial shrub; upright, outwardly spreading and mounding plant habit; vigorous growth habit.

*Branching habit.*—Freely branching habit with about seven primary lateral branches; pinching (removal of terminal apices) will enhance lateral branch development.

*Plant height.*—About 60 cm.

*Plant diameter* (*area of spread*).—About 65 cm.

Lateral branch description:

*Length.*—About 20 cm.

*Diameter.*—About 2 mm.

*Internode length.*—About 1.5 cm.

*Texture.*—Pubescent.

*Color, spring.*—Close to 147D tinged with close to 34A.

*Color, summer.*—Close to 147D.

Foliage description:

*Arrangement.*—Alternate or whorled, simple.

*Length.*—About 4 cm.

*Width.*—About 2.5 cm.

*Shape.*—Ovate.

*Apex.*—Acute.

*Base.*—Cuneate.

*Margin.*—Doubly serrate.

*Texture, upper and lower surfaces.*—Pubescent.

*Venation pattern.*—Pinnate.

*Color, spring.*—Developing leaves, upper and lower surfaces: Close to 34A. Fully expanded leaves, upper and lower surfaces: Close to 8A; venation, similar to surface color.

*Color, summer.*—Developing leaves, upper and lower surfaces: Close to 177B to 177C. Fully expanded leaves, upper surface: Close to 151A; venation, similar to surface color. Fully expanded leaves, lower surface: Close to 145A; venation, similar to surface color.

*Petiole.*—Length: About 4 mm. Diameter: About 1 mm. Texture, upper and lower surfaces: Smooth, glabrous. Color, upper and lower surfaces: Close to 144C.

Flower description:

*Flower appearance/arrangement.*—Single rotate flowers arranged in compound corymbs; freely flowering habit with usually about 200 flowers per inflorescence; flowers face mostly upright.

*Natural flowering season.*—Continuous flowering from the late spring through the summer in Grand Haven, Mich.

*Fragrance.*—Mildly fragrant; sweet, pleasant.

*Inflorescence height.*—About 3.5 cm.

*Inflorescence diameter.*—About 4 cm to 8 cm.

*Flower diameter.*—About 5 mm.

*Flower length* (*height*).—About 5 mm.

*Flower bud.*—Length: About 2 mm. Diameter: About 2 mm. Shape: Globose. Color: Close to 66A.

*Petals.*—Quantity per flower: Single whorl of five. Length: About 2 mm. Width: About 2 mm. Shape: Orbicular. Apex: Obtuse. Margin: Entire. Texture, upper and lower surfaces: Smooth, glabrous. Color: When opening, upper and lower surfaces: Close to 66C. Fully opened, upper and lower surfaces: Close to 66D.

*Sepals.*—Quantity per flower: Single whorl of five. Length: About 1 mm. Width: About 1 mm. Shape: Rounded. Apex: Acute. Base: Truncate. Margin:

Entire. Texture, upper and lower surfaces: Smooth, glabrous. Color: When opening, upper surface: Close to 186A. When opening, lower surface: Close to 185A. Fully opened, upper surface: Close to 145A; towards the margins, close to 58A. Fully opened, lower surface: Close to 58A.

*Peduncles.*—Length: About 1.6 cm. Diameter: About 1 mm. Strength: Strong. Texture: Smooth, glabrous. Color: Close to 146D.

*Pedicels.*—Length: About 3 mm. Diameter: About 1 mm. Strength: Strong. Texture: Smooth, glabrous. Color: Close to 146D.

*Reproductive organs.*—Androecium: Quantity per flower: About 18. Anther shape: Globose. Anther length: About 0.25 mm. Anther color: Close to 64A. Amount of pollen: Scarce. Pollen color: Close to 8D. Gynoecium: Quantity per flower: One. Pistil length: About 1 mm. Style length: About 0.75 mm. Style color: Close to 60B. Stigma appearance: Globose. Stigma color: Close to 60B. Ovary color: Close to 182C.

*Seeds.*—Length: About 1 mm. Diameter: About 0.5 mm. Color: Close to 161C.

Garden performance: Plants of the new *Spiraea* have been observed to have good garden performance and to tolerate rain, wind and temperatures ranging from about −29C to about 37° C.

Pathogen/pest resistance: Plants of the new *Spiraea* have not been observed to be resistant to pathogens and pests common to *Spiraea*.

It is claimed:

1. A new and distinct *Spiraea* plant named 'Tracy' as illustrated and described.

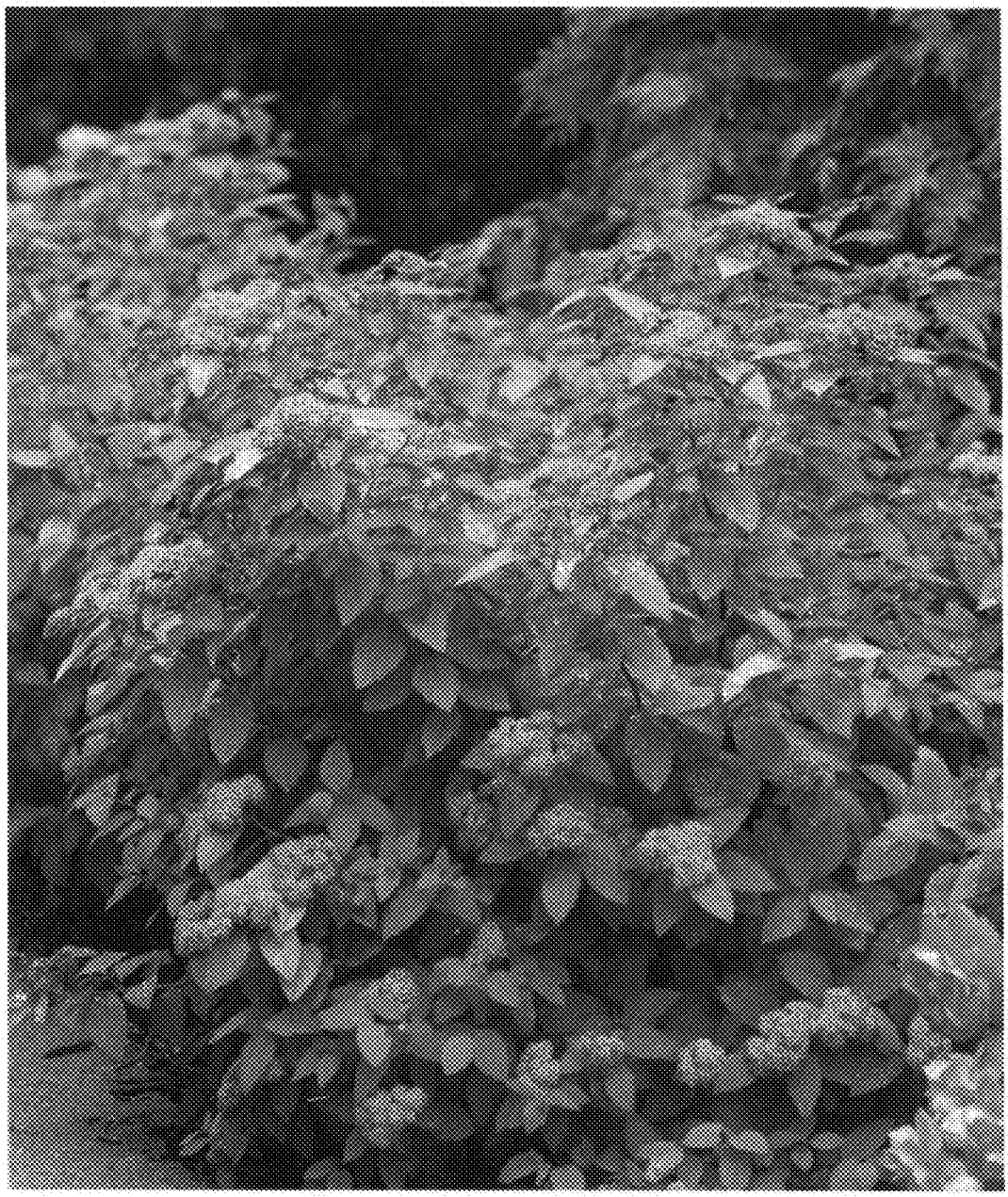

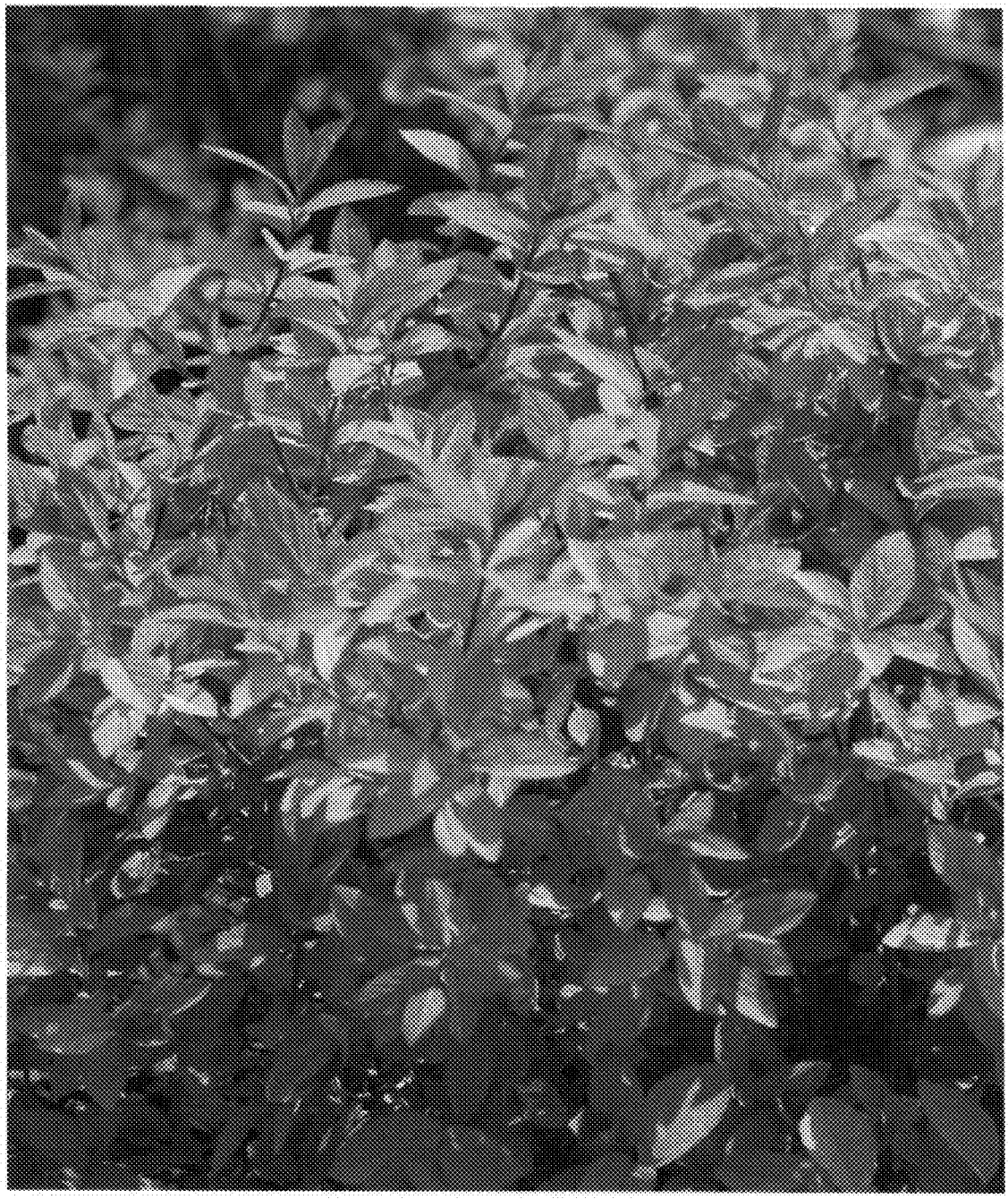

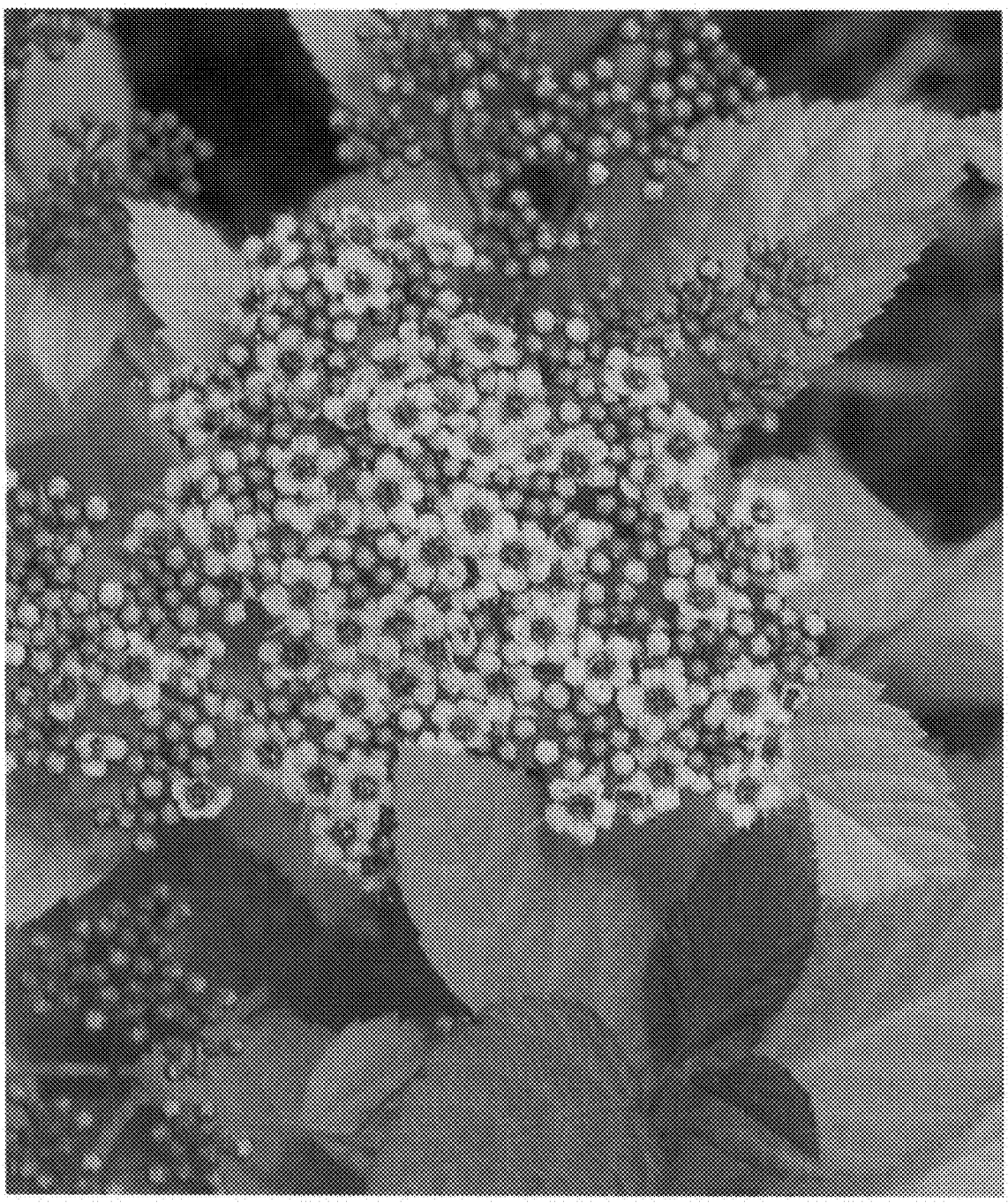

* * * * *